United States Patent [19]

Alfrey et al.

[11] 4,200,613
[45] Apr. 29, 1980

[54] RADIOIMMUNOASSAY APPARATUS

[75] Inventors: Clarence P. Alfrey, Houston; Donald B. Bedford, New Braunfels, both of Tex.

[73] Assignee: Ramco Laboratories Inc., Houston, Tex.

[21] Appl. No.: 896,176

[22] Filed: Apr. 14, 1978

Related U.S. Application Data

[63] Continuation of Ser. No. 803,366, Jun. 3, 1977, abandoned.

[51] Int. Cl.$^2$ .............................................. G01N 33/16
[52] U.S. Cl. .................................... 422/71; 23/230 B; 23/920; 422/58; 422/57; 435/300
[58] Field of Search ................ 23/259, 253 R, 230 B, 23/292; 195/127; 424/1, 12

[56] References Cited

U.S. PATENT DOCUMENTS

| | | | |
|---|---|---|---|
| 3,356,462 | 12/1967 | Cooke et al. | 23/292 |
| 3,646,346 | 2/1972 | Catt | 424/12 X |
| 3,646,346 | 2/1972 | Catt | 23/230 B |
| 3,650,306 | 3/1972 | Lancaster | 23/259 |
| 3,790,663 | 2/1974 | Garrison | 424/12 |
| 3,867,517 | 2/1975 | Ling | 23/230 B |
| 3,899,298 | 8/1975 | Szezesniak | 23/253 R |
| 4,053,284 | 10/1977 | Posch | 23/292 |

OTHER PUBLICATIONS

Cook, et al. The Amer. Jour. of Clin. Nutrition, vol. 27, pp. 681-687 (1974).
Miles et al., Nature, vol. 219, pp. 186-189 (1968).
Jacobs et al., British Med. Jour. vol. 4, pp. 206-208 (1972).
Lipschitz et al., The New Eng. Jour. of Med., vol. 290, No. 22 pp. 1213-1216 (1974).
Addison et al., Journal of Clinical Pathology, vol. 25 pp. 326-329 (1972).
Miles et al., Analytical Biochem., vol. 61, pp. 209-224 (1974).
Abbott Labs, Diagnostics Div., "Hepatitus Associated Antibody Auria II-125," Radioimmunoassay for the Detection of Hepatitus B Antigen (1975).
Miles et al., Biochem. Jour., vol. 108, pp. 611-618 (1968).

Primary Examiner—R. E. Serwin
Attorney, Agent, or Firm—Arnold, White & Durkee

[57] ABSTRACT

A coated bead, a gripper for rotatably engaging the bead, a carrier for carrying at least one gripper, test tray bearing at least one reaction chamber and an agitator for agitating the carrier in relation to the test tray are disclosed.

15 Claims, 7 Drawing Figures

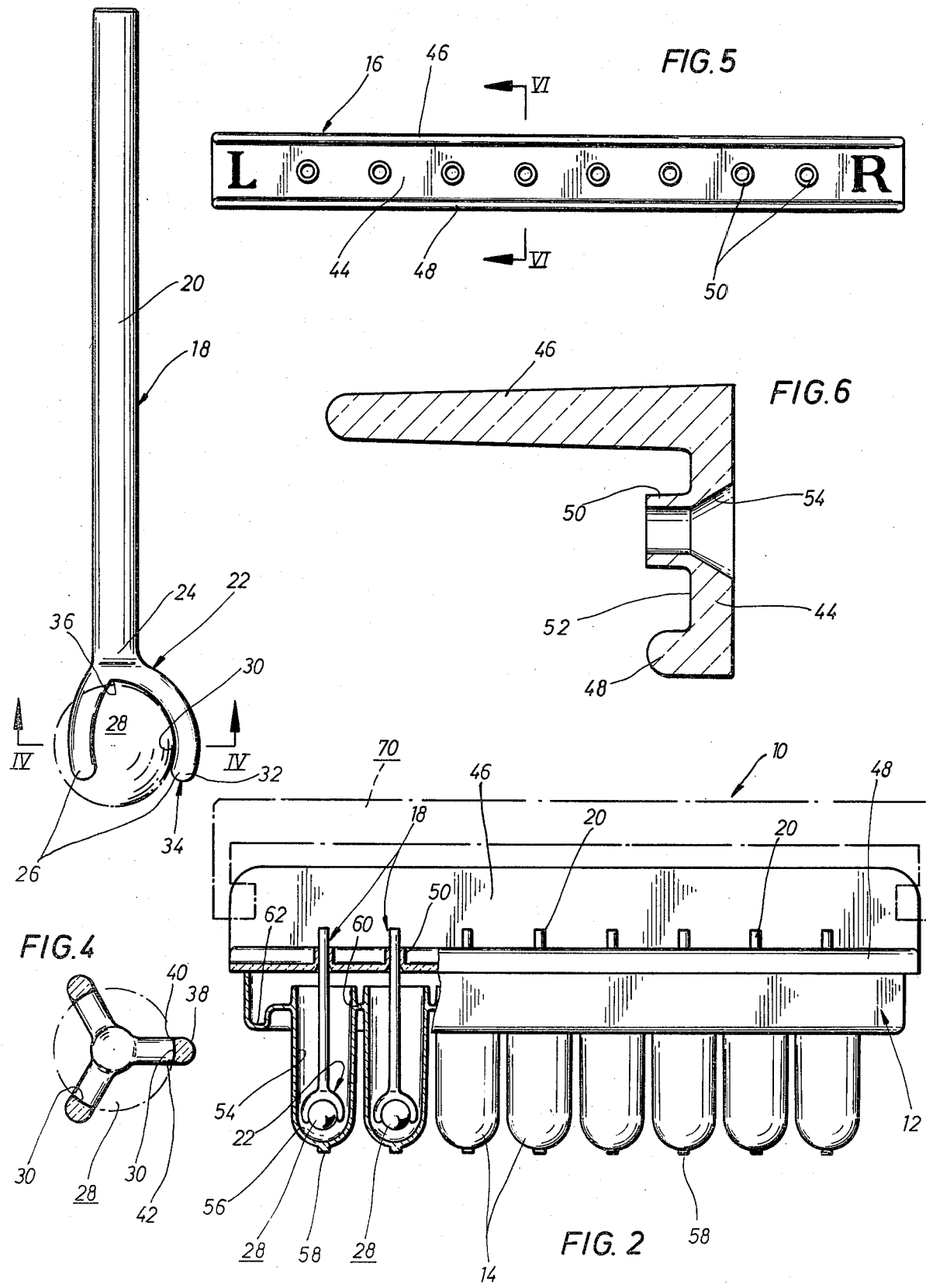

RADIOIMMUNOASSAY APPARATUS

This is a continuation of application, Ser. No. 803,366, filed June 3, 1977 and now abandoned.

BACKGROUND OF THE INVENTION

The present invention relates to a diagnostic apparatus having utility in the radioimmunoassay of antigens and their antibodies. More particularly, the invention relates to an apparatus for a two-site immunoradiometric assay for serum ferritin in human blood samples.

Ferritin is a high molecular weight protein functioning primarily as a situs for iron storage. Ferritin can be found in almost every solid tissue of the human body, but it appears principally in the cytoplasm of hepatic and reticuloendothelial cells. Prior to about 1972, it had been assumed that ferritin only existed in extracellular fluid under abnormal conditions. It has since been discovered that the concentration of serum ferritin directly correlates with the content of iron in body stores in normal human beings. Thus, the measurement of serum ferritin levels provides an effective method by which the status of body iron stores may be evaluated and clinical diagnoses made therefrom. For example, an accurate measurement of the serum ferritin level will enable a clinician to differentiate between that anemia caused by iron depletion and other forms of anemia.

Inasmuch as ferritin is an antigenically active macromolecule, the presence of ferritin can be detected by techniques which have been developed in the past for detecting various other antigenic materials. The radioimmunoassay procedure is an example of such a technique.

Addison et al, *Journal of Clinical Pathology*, Volume 25, pages 326–329 (1972) disclose a technique wherein human blood serum is treated with soluble purified radioactive ferritin antibodies. The radioactive complex produced remains in solution while unused radioactive antibodies, i.e., those which do not link up with the antigen, are removed by a second reaction with a solid phase antigen.

Miles et al, *Analytical Biochemistry*, Volume 61, pages 209–224 (1974) suggests an improvement in this technique wherein the ferritin is first insolubilized and thereafter is made to react with soluble labeled antibody. The labeled complex is thus insoluble and any unreacted labeled antibody can be washed away. It will be appreciated that the amount of ferritin present will be directly proportional to the radioactivity in solid phase.

Solid phase radioimmunoassay of antigens is believed to have been developed by Catt (see, e.g., U.S. Pat. No. 3,646,346 to Catt) and others (see for example, U.S. Pat. No. 3,790,663 to Garrison et al). Basically, the prior art teaches the solid phase antibodies are coated on a polystyrene substrate. The substrates are then placed in contact with serum containing ferritin and permitted to stand for a period of time to enable reaction to occur. After an incubation period, the substrates are washed, dried, and a radioactive count measurement is taken. The measurement is compared with standard values for different serum ferritin concentration levels.

More recently, a two-site immunoradiometric assay for serum ferritin has been developed. This new test is basically a two stage reaction. In the first stage, human serum ferritin is bonded to a solid-phase anti-human ferritin. In the second stage, a purified, radiolabeled anti-human ferritin is bound to the first stage reaction product. Then the solid phase is washed and counted in a radiation counter. The concentration of serum ferritin may be calculated by comparing the unknown with a simultaneously run standard sample.

Apparatus for performing a quantitative radioimmunoassay have been somewhat varied. The present invention is directed to an improvement over apparatus which includes the following components. Firstly there is provided a water insoluble polymeric substrate fashioned as a sphere or bead. This bead is coated with a previously formed human ferritin antibody. After the beads have been prepared, the beads are washed with deionized water.

Later, each bead is washed in a container such as a beaker. After the washing is completed, the container is aspirated to remove the rinsing water. Immediately after aspiration of the water, a bead would have to be placed in a test tube having a diluted sample of patient serum and a test tube containing the test standard. The beads would remain in the test tubes at room temperature for six hours or for sixteen hours at 4° C. Alternatively, the test tubes could be covered and placed on a horizontal rotating table and shaken for approximately two hours at a moderate speed at room temperature.

In the prior art, after incubation, the reaction solution is aspirated from the test tube bearing the patient sample and the test tube bearing the standard. Then each bead is washed twice with a special washing solution. This washing solution is sprayed onto the bead and is almost immediately thereafter aspirated by an apparatus especially adapted for such use. Each bead is washed twice with approximately one minute between washings. The test tubes must be aspirated twice to remove any liquid that may have drained from the sides of the test tubes.

After washing and aspirating, the radiolabeled antibody is introduced onto the beads in the test tubes. The test tubes are then refrigerated at 4° C. for sixteen hours. Alternatively, the test tubes can be covered and shaken on a horizontal shaking apparatus for 2 hours at a moderate speed at room temperature.

After this second incubation, the radioactive solution is aspirated from each test tube utilizing a special apparatus. This relatively complex device is used to wash each bead three times with a washing solution. The washing solution, of course, must be aspirated after each wash. After the last wash, the test tubes are required to remain stationary for an additional minute to give liquid on the side of the test tube an opportunity to drain to the bottom. This additional fluid should be aspirated.

Each of the beads is then removed from their respective test tubes and introduced into special counting tubes which were not used in the assay. The counting tubes are introduced into a gramma radiation counter set to detect the labeling isotope. The beads are counted for a time appropriate for adequate statistical significance, and the appropriate calculations are made in a now well-known manner to provide a quantitative determination of iron ferritin in the patient.

While such arrangements have exhibited at least a degree of utility in radioimmunoassay, room for significant improvement remains. The beads utilized in at least some known iron ferritin analyses are $\frac{1}{4}''$ in diameter and are relatively difficult to handle. Handling by a pathologist or laboratory technician introduces the risk of contamination both to the test sample and to the personnel. Because the $\frac{1}{4}''$ diameter beads are difficult to handle, they may be dropped thus necessitating repeating the time-consuming first stage and second stage incubation periods. This time delay may have adverse consequences to the patient and results generally in an inefficient laboratory operation.

Utilizing known apparatus, the beads would require handling after both the first and second phase incubations have occurred. If a test sample were spoiled at the second phase of the procedure, several days may be required to repeat the procedure.

Of independent significance, is the relatively complex equipment required to wash and aspirate each test tube containing a test bead. In order to achieve satisfactory washing, the washing procedure must be repeated once and is preferably repeated another time. Aspiration is required between washings, and both a pressure pump and a suction pump are required. The pressure pump is required to introduce the washing solution into each test tube, and a suction pump is required to draw the washing solution out of the test tube through a specially adapted conduit. It will be appreciated that in the event of a failure of the relatively expensive washing or aspirating equipment, the assay might be terminated or spoiled. In addition, it is believed that with washing and aspirating, even three times and with a specially formulated washing solution, there may not be an adequate washing of each bead.

The problems enumerated in the foregoing are not intended to be exhaustive but rather are among many which tend to impair the effectiveness of previously known radioimmunoassay apparatus. Other noteworthy problems may also exist; however, those presented above should be sufficient to demonstrate that radioimmunoassay apparatus appearing in the art have not been altogether satisfactory.

OBJECT AND SUMMARY OF PREFERRED EMBODIMENT

Recognizing the need for an improved radioimmunoassay apparatus, it is, therefore, a general object of the present invention to provide a novel radioimmunoassay apparatus which minimizes or reduces the problems of the type previously noted.

It is a more particular object of the present invention to provide a novel ferritin assay diagnostic kit which eliminates or substantially minimizes direct contact with test beads which form the substrate for solid phase human ferritin antibodies.

It is another object of the present invention to provide a novel ferritin assay diagnostic kit which is not dependent upon complex washing or aspirating apparatus.

It is yet another object of the present invention to provide a novel ferritin assay diagnostic kit which improves control and facilitates handling of coated beads.

It is still another object of the present invention to provide a novel ferritin assay diagnostic kit which improves efficiency of laboratory operations and minimizes test repeats.

It is yet still another object of the present invention to provide a novel ferritin assay diagnostic kit which improves the affectiveness of a washing and wiping of coated beads.

An apparatus for performing a quantitative radioimmunoassay according to a presently preferred embodiment of the invention intended to substantially accomplish the foregoing objects includes a bead for carrying a dry antibody, a gripper for gripping the bead, a carrier for carrying at least one gripper, and a reaction chamber or test tube. The gripper is comprised of an elongate handle portion and a clasp portion preferrably in the form of a trident. The particular arrangement of the trident facilitates a spinning of the bead while engaged by the gripper. The carrier includes a base and preferably a plurality of spaced apart collars carried thereon for receiving the elongate handle portion of the gripper. In preferred form, the reaction chambers are arranged in a 4×8 matrix and are spaced-apart to correspond to the spacing of the collars of the carrier.

Examples of the more important features of this invention have thus been outlined rather broadly in order that the detailed description thereof that follows may be better understood and in order that the contribution to the art may be better appreciated. There are, of course, additional features of the invention that will be described hereinafter and which will also form the subject matter of the claims appended hereto.

These features will become apparent with reference to the following detailed description of a preferred embodiment in connection with the accompanying drawings, wherein like referenced numerals have been applied to like elements.

BRIEF DESCRIPTION OF THE DRAWINGS

FIG. 2 is a partial-sectional view taken along section lines II—II in FIG. 1;

FIG. 3 is a plan view of a gripper with a bead within the clasp thereof according to the apparatus of the present invention;

FIG. 4 is a sectional view taken along section lines IV—IV in FIG. 3;

FIG. 5 is a plan view of a carrier for carrying the gripper of FIG. 3;

FIG. 6 is an enlarged sectional view of the carrier of FIG. 5 taken along section lines VI—VI in FIG. 5.

DETAILED DESCRIPTION OF A PREFERRED EMBODIMENT

Figure 1:
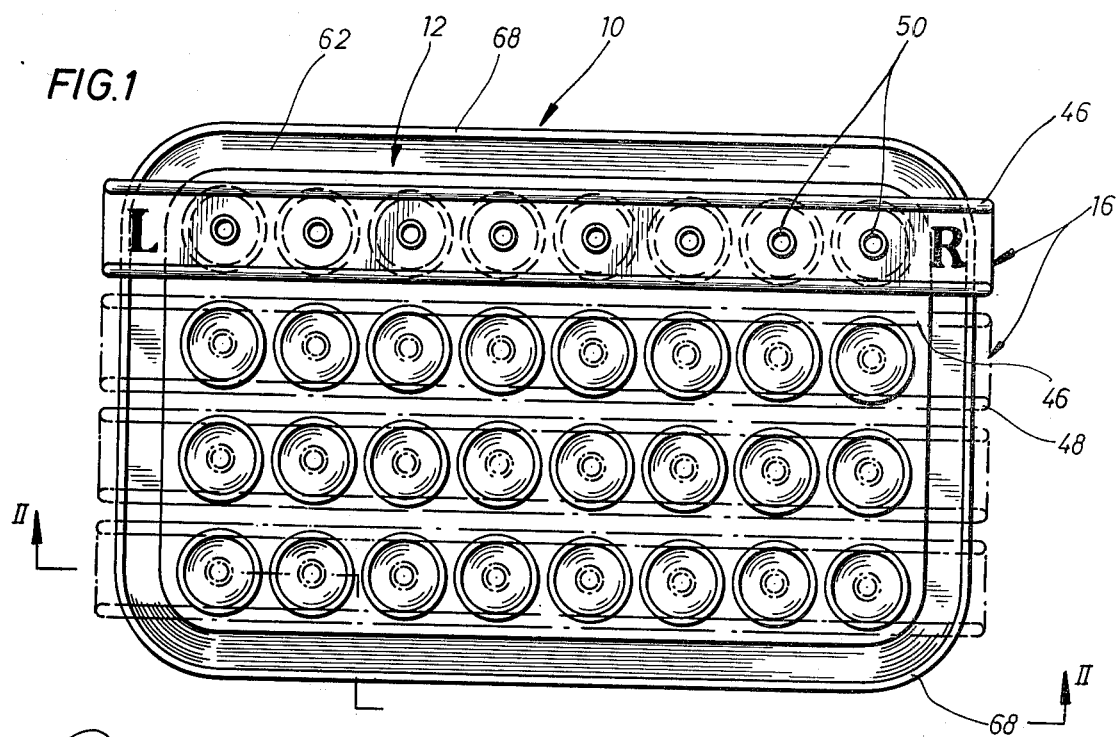
FIG. 1 is a plan view of the apparatus of the present invention.

With particular reference now to FIGS. 1 and 2 there may be seen a radioimmunoassay (RIA) apparatus in accordance with the present invention.

The RIA apparatus 10 is comprised of a test tray 12 having a plurality of reaction chambers 14 arranged preferably in a 4×8 matrix. A plurality of gripper carriers 16 are arranged along the 8-unit rows of the test tray 12. Each carrier 16 is arranged to carry a plurality of bead grippers 18.

Each bead gripper 18 is comprised of an elongate handle portion 20 and a clasp or trident 22 at one end 24 of the handle portion 20 (see FIGS. 3 and 4). The trident 22 is comprised of three resilient or spring-like fingers 26 which are arranged to engage a coated bead 28. Each finger 26 extends from the end 24 of the handle portion 20 to a point beyond a diameter of the bead transverse the longitudinal axis of the handle. That is, each of the fingers extends beyond halfway around the bead 28. Each finger 26 has an interior surface 30 which is contoured to correspond to the surface of the bead 28. The distal end 32 of each finger 26 has a rounded camming surface 34. A base 36 of the trident, i.e., the zone where the fingers 26 intersect, is arranged to lie out of contact with the surface of the bead 28. An outer surface 38 of each finger intersects the intercontoured surface at two edges 40, 42 which extend from about the camming surface 34 almost to the trident base 36.

When it is desired to grip a bead 28 with the gripper 18, the gripper is held by the handle portion 20 and the trident 22 is positioned over the bead. The gripper is then pressed towards the bead. This pressing force causes each of the fingers 26 to be cammed outwardly by their respective camming surfaces 34. As the fingers travel over the surface of the bead, they are urged outwardly until the plane of the transverse diameter is intersected whereupon the fingers begin to converge. As the fingers begin to converge, they tend to "snap" the bead toward the base 36 of the trident.

With the bead 28 thus gripped or engaged by the gripper 18, the bead may be manipulated with facility. The bead may be washed by positioning the bead (held with the gripper) beneath a stream of flowing water. The inside contoured surfaces 30 of the fingers 26 and the displacement of the trident base 36 out of contact with the bead facilitate a spinning of the bead when placed beneath a stream of flowing liquid. Moreover, the edges 40, 42 of the fingers 26 tend to wipe the bead as the bead rotates. This wiping action along with the rotation of the bead provides an improved washing on all surfaces including those lying initially beneath each finger 26 and beneath the trident base 36.

As may be seen in FIGS. 5 and 6, each carrier 16 comprises a base portion 44, a handle 46 which extends along the entire length of the base portion 44, and a lip 48 which also extends along the entire length of the base portion 44. At locations along the base portion 44 there are provide a plurality of gripper handle-engaging collars 50. Each collar 50 extends slightly above a top surface 52 of the base 44. Fashioned coaxially with respect to each collar 50 is a chamfer 54. The diameter of each collar 50 is selected to provide an interference fit with the gripper handle 20. As may be seen in FIG. 2, a series of bead grippers 18 may be inserted into a plurality of collars 50 to facilitate handling several grippers at one time.

As will be appreciated from FIGS. 1 and 2, the collars 50 are preferably arranged in the carrier 16 to correspond to the openings in a row of eight reaction chambers 14 in the test tray 12. The base 44 of the carrier 16 is of a length sufficient to accommodate an entire 8-unit row of reaction chambers 14. However, it will be appreciated that a single carrier could be provided which was of a length appropriate to position a collar above each reaction chamber in 8-unit rows of adjacent test trays. In addition, the carrier could be of a width appropriate to facilitate handling more than one row of reaction chambers in a test tray. That is, a single carrier might be provided to accommodate all of the reaction chambers 14 in the test tray 12 of FIG. 1.

In preferred form the carrier 16 will provide collars which correspond to a single row of reaction chambers 14 in a single test tray 12. It has been found that providing a signal or indicator of orientation for the carrier in addition to its structural components is desirable. In carrying out a procedure with the RIA apparatus of the present invention, proper labeling of each reaction chamber 14 and/or bead 28 is essential. Therefore, the letters "L" and "R", corresponding to "left" and "right" are preferably embossed or printed or otherwise affixed to each carrier 16 (see FIG. 5).

Figure 7:
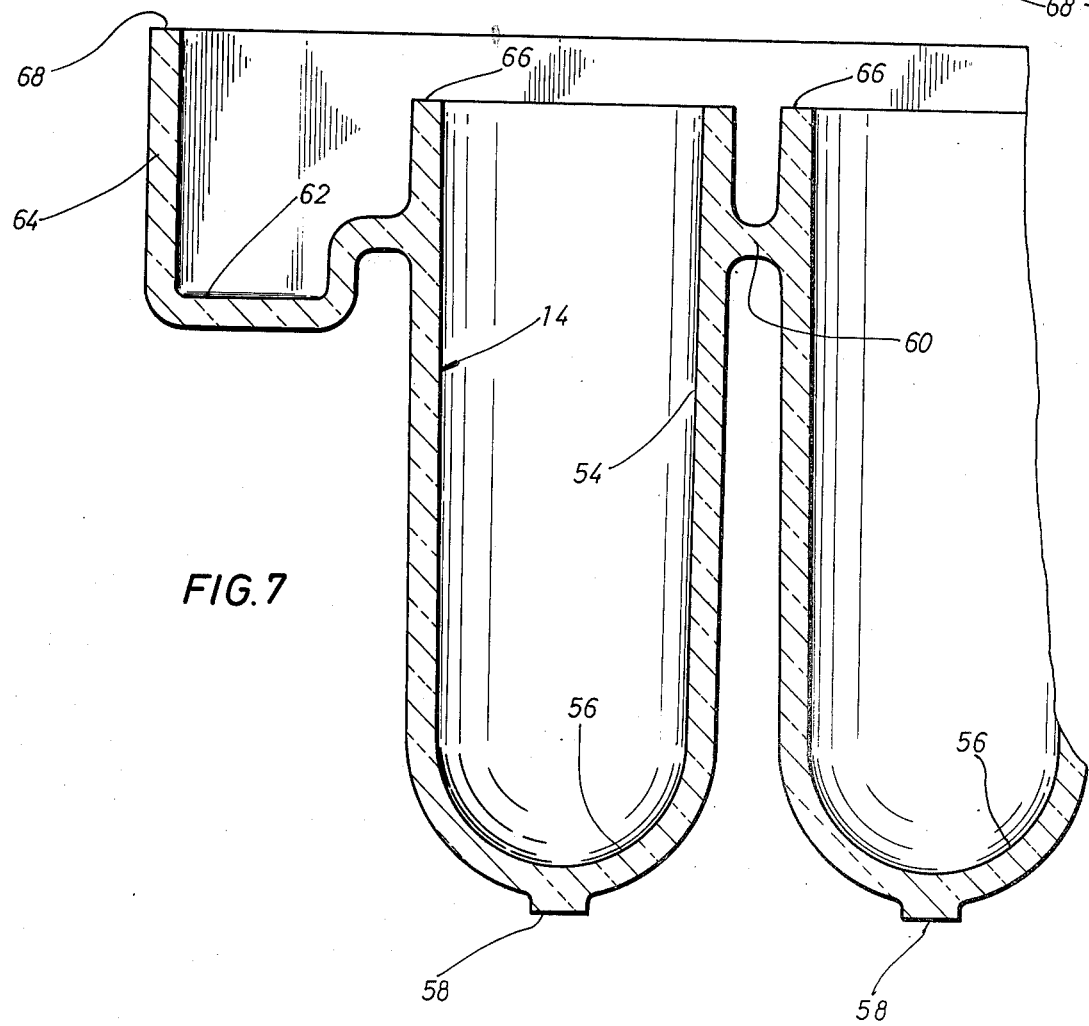
FIG. 7 is a detailed sectional view of the test tray depicted in FIG. 1.

As noted above, the test tray 12 comprises a matrix of reaction chambers 14. Each reaction chamber 14 is defined by a generally cylindrical wall 54 and a curved bottom 56 (see FIG. 7). The curved bottom portion 56 is provided with a foot 58. The generally cylindrical wall 54 of each reaction chamber 14 tapers slightly over the length of the reaction chamber. This taper is in the order of a half degree or so. The reaction chambers 14 are interconnected with a web 60. A peripheral channel 62 is provided below the level of the web 60 to facilitate control of spillage. A peripheral lip 64 which forms an outer wall of the peripheral channel 62 may extend to or above the plane of the tops 66 of the reaction chambers 14. An upper edge 68 of the peripheral lip 64 is operable to support each carrier 16 when it is desired to position the beads within the reaction chambers as shown in FIG. 2.

Each bead 28 is preferably fashioned from a water insoluble polymeric material. This polymeric material forms the substrate for previously formed human ferritin antibodies. The substrate should be of a material which readily adsorbs the proteinaceous antibody material. It is known that most organic polymeric materials meet this criterion.

Examples of organic polymers suitable for the manufacture of beads 28 are hydrocarbon polymers such as polystyrene, polyethylene, polypropylene, polybutylene, butyl rubber and other synthetic rubbers, as well as polyesters, polyamides, vinyl and acrylic polymers such as polyvinyl chloride, and polymethel methacrylate, cellulose and cellulose derivatives such as cellulose acetate. In general, any organic polymeric material which adsorbs protein in relatively large amounts will be acceptable. The preferred substrate is impact grade polystyrene. The coated beads are prepared by dipping them into the antigen or antibody solution desired and following a known procedure for suitable adsorption.

In operation, the apparatus may be utilized to perform a two-site immunoradiometric assay as follows. An unknown sample of human serum to be tested for ferritin content is introduced into an appropriately labeled reaction chamber 14. A ferritin standard is similarly introduced into another appropriately labeled reaction chamber 14.

Coated plastic beads 28 required for the assay preferably are placed in a petri dish (not shown) containing distilled water. A gripper 18 is then placed over the submerged or partially submerged bead 28 to engage the bead. After engagement of the bead, the pathologist or technician has absolute control over the bead, and the chances of spoiling the test are minimized. With the required number of beads engaged, the grippers may be inserted into the collars 50 on the carrier 16. As noted above, the grippers are interference fit into the collars.

The carrier (with the grippers inserted into the collars) may be placed over the reaction chambers, and the beads are submerged in the serum samples.

The reaction chambers may be permitted to stand at room temperature for six hours or at 4° C. for sixteen hours. Alternatively, the test tray may be placed on a horizontal rotating table and shaken for two hours at a moderate speed at room temperature.

It has been found desirable in some instances to position the test tray 12 on a stationary surface and connect the carrier 16 to a vibrator or agitation apparatus schematically depicted at 70 (see FIG. 2) to facilitate incubation. Alternatively, the carrier 16 may be supported by a fixed object, and the test tray 12 may be vibrated. In any event, it will be appreciated that the apparatus of the present invention facilitates improved agitation of the beads with improved results in the quality of incubation.

After a first stage incubation, the carrier 16 may be lifted away from the test tray 12, and the grippers 18 may be placed under a stream of, say, distilled water to wash the beads. As noted above, the beads 28 will rotate in the stream, and a wiping action will be produced by the edges 40, 42 of the fingers 26.

The carrier 16 is then positioned over the test tray to introduce the beads 28 into a different row of reaction chambers 14 which contain a radio-labeled antibody or antisera. A second stage incubation is facilitated by refrigerating the test tray 12 with the beads in the reaction chambers at 4° C. for sixteen hours. Alternatively, the incubation may be stimulated by agitating either the test tray 12 or the carrier 16 for two hours at a moderate speed at room temperature.

Then each carrier 16 is removed from the test tray, and the beads are again rinsed under a stream of distilled water. Then each gripper 18 is removed from the carrier. The gripper may be used to move the bead to a counting tube (not shown) where the bead 28 will be forced out of the trident either manually or with an appropriate instrument. The beads are then counted in a gamma radiation counter set to detect the labeling isotope. All beads are counted for the amount of time required for adequate statistical results. The appropriate calculations are then made to evaluate the test results.

SUMMARY AND SCOPE OF THE INVENTION

According to the present invention there is provided an apparatus for performing a quantitative analysis for determining the concentration of serum ferritin in human blood. According to the invention, at least for a portion of the assay, a water insoluble organic polymeric bead such as a polystyrene bead, is held by a gripper which enables the bead to be rotated during washing. A group of such grippers are treated at one time by means of a special carrier.

Agitation to enhance incubation may be facilitated by vibrating either the test tray in relation to the stationary grippers or vice versa. It will, of course, be appreciated that the test tray, carrier, gripper and bead are fashioned from materials having sufficient strength to withstand the forces of agitation imposed during incubation.

In constructing a radioimmunoassay apparatus according to the present invention, certain significant advantages are provided. In particular, the test beads may be manipulated without direct contact with the beads and without a resulting likelihood of contamination. Moveover, the beads are securely gripped by the gripper of the present invention which greatly reduces the possibility of dropping or misplacing the bead.

In addition, entire rows of beads may be handled at one time with the present apparatus. This results in increased laboratory efficiency and minimizes repeat testing.

Further modifications and alternative embodiments of the apparatus of this invention will be apparent to those skilled in the art in view of this description. Accordingly, this description is to be construed as illustrative only and is for the purpose of teaching those skilled in the art the manner of carrying out the invention. It is to be understood that the forms of the invention herewith shown and described are to be taken as the presently preferred embodiment. Various changes may be made in the shape, size and arrangement of parts. For example, the trident portion of the gripper may be comprised of four, five, or more finger-like members, equivalent materials may be substituted for those described herein, some parts may be reversed, and certain features of the invention may be utilized independently of the use of the other features, all as would be apparent to one skilled in the art after having the benefit of this description of the invention.

What is claimed is:

1. Apparatus for performing a quantitative radioimmunoassay comprising:
   a bead for carrying a dry antibody;
   a gripper for gripping said bead, said gripper comprising
     an elongate handle portion, and
     a clasp portion;
   a carrier for carrying said gripper, said carrier comprising
     a base portion
     a plurality of spaced apart collars carried by said base portion and for receiving therethrough said elongate handle portion; and
   a reaction chamber for receiving said bead when said bead is gripped by said gripper and having support means to support said carrier when said gripper is carried by said carrier.

2. The apparatus of claim 1 wherein said clasp portion comprises a finger, said finger having an interior surface which is contoured to conform to a surface of said bead.

3. The apparatus of claim 2 wherein said finger further comprises an end having a camming surface to deflect said finger away from said bead when said gripper is urged towards said bead.

4. The apparatus of claim 1 wherein said bead is rotatably held by said gripper.

5. The apparatus of claim 1 wherein said apparatus comprises a plurality of said reaction chambers, said chambers being arranged in a matrix.

6. The apparatus of claim 5 wherein said collars are equidistantly spaced and linearly aligned on said base portion.

7. The apparatus of claim 6 wherein said collars are axially aligned with a row of said reaction chambers.

8. The apparatus of claim 1 and further including agitation means for agitating said carrier relative to said reaction chamber.

9. The apparatus of claim 1 wherein said clasp portion comprises a finger, said finger having a wiping edge, said bead being rotatably held by said gripper, said wiping edge being operable to wipe the surface of said bead when said bead is rotated.

10. The apparatus of claim 9 and further including agitation means for agitating said carrier relative to said reaction chamber.

11. Apparatus for performing a quantitative radioimmunoassay comprising:
    a bead for carrying a dry antibody; and
    a gripper for gripping said bead, said gripper comprising
      an elongate handle portion, and
      a clasp portion.

12. The apparatus of claim 11 wherein said clasp portion comprises a finger, said finger having an interior surface which is contoured to conform to a surface of said bead.

13. The apparatus of claim 12 wherein said finger further comprises an end having a camming surface to deflect said finger away from said bead when said gripper is urged towards said bead.

14. The apparatus of claim 11 wherein said bead is rotatably held by said gripper.

15. The apparatus of claim 11 wherein said clasp portion comprises a finger, said finger having a wiping edge, said bead being rotatably held by said gripper, said wiping edge being operable to wipe the surface of said bead when said bead is rotated.

* * * * *